United States Patent [19]

Kingsman et al.

[11] Patent Number: 5,739,007
[45] Date of Patent: Apr. 14, 1998

[54] HYBRID GAL10/PGK YEAST PROMOTER

[75] Inventors: Susan Mary Kingsman, Oxon; Diane Joan Cousens, Kent; Mark Julian Wilson, Nottingham; Edward Hinchliffe, Burton-on-Trent, all of United Kingdom

[73] Assignee: Delta Biotechnology Limited, Nottingham, United Kingdom

[21] Appl. No.: 119,926

[22] Filed: Sep. 10, 1993

Related U.S. Application Data

[63] Continuation of Ser. No. 853,865, Mar. 20, 1992, which is a continuation of Ser. No. 577,815, Sep. 4, 1990, abandoned, which is a continuation of Ser. No. 89,987, Aug. 27, 1987, abandoned.

[30] Foreign Application Priority Data

Aug. 29, 1986 [GB] United Kingdom ........... GB 86 20926

[51] Int. Cl.$^6$ .................. C12P 21/06; C12N 1/19; C12N 15/11; C12N 15/81
[52] U.S. Cl. .................. 435/69.1; 435/71.1; 435/254.2; 435/320.1; 536/24.1
[58] Field of Search .................. 435/69.1, 71.1, 435/91.32, 91.4, 172.1, 172.3, 254.2, 254.21, 320.1; 536/24.1

[56] References Cited

U.S. PATENT DOCUMENTS 4,803,164  2/1989  Hitzeman et al. .................. 435/69.3

OTHER PUBLICATIONS

Guarente & Mason; "Heme Regulates Transcription of the CYC1 Gene of *S. cerevisiae* via an Upstream Activation Site" (1983) *Cell* 32, pp. 1279-1286.

Corraggio et al; "Transcription and expression of zein sequences in yeast under natural plant or yeast promoters" (1986) *EMBO J* 5, pp. 459-465.

Tuite et al; "Regulated high efficiency expression of human interferon-alpha in *Saccharomyces cerevisiae*" (1982) *EMBO J* 1, pp. 603-608.

Mellor et al; "Efficient synthesis of enzymatically active calf chymosin in *Saccharomyces cerevisiae*" (1983) *Gene* 24, pp. 1-14.

Dobson et al; "Conservation of high efficiency promoter sequences in *Saccharomyces cerevisiae*" (1982) *Nucl Acids Res* 10, pp. 2625-2637.

Guarente & Hoar; "Upstream activation sites of the CYC1 gene of *Saccharomyces cerevisiae* are active when inverted but not when placed downstream of the 'TATA box'" (1984) *PNAS USA* 81, pp. 7860-7864.

Guarente et al. (1982), PNAS (USA), vol. 79: pp. 7410-7414.

Hawkins et al. (1982), Gene, vol. 19: pp. 55-58.

Bitter et al. (1984), PNAS (USA), vol. 81: pp. 5330-5334.

Primary Examiner—George C. Elliott
Assistant Examiner—Terry A. McKelvey

[57] ABSTRACT

A hybrid yeast promoter comprising constituents of the 5' non-coding PGK region and, as an upstream activation sequence, the upstream activitation sequence of the GAL10 gene of *Saccharomyces cerevisiae*, and which does not contain the endogenous PGK upstream activation sequence. Preferably the GAL10 upstream activation sequence is provided at a site from which the PGK upstream activation sequence has been deleted. The hybrid promoter confers galactose regulation of gene transcription.

13 Claims, 8 Drawing Sheets

BAL 31 deletion series of pDB4

| Deletion/<br>Plasmid | -20 | | -10 | | -1 | | |
|---|---|---|---|---|---|---|---|
| pDB4 | TTTACAACAA | | ATATAAAACA | | ATGTCTTTAT | | CTTCA |
| -8 (pKV47, pKV49, pKV50) | TTTACAACAA | | ATACAAAAGA | | <u>TCTTTTG</u> | | |
| +4 (pKV51, pKV61, pKV62) | TTTACAACAA | | ATATAAAACA | | ATGTCAAAAG | | <u>ATCTTTTG</u> |
| +5 (pKV52, pKV63, pKV64) | TTTACAACAA | | ATATAAAACA | | ATGTCCAAAA | | <u>GATCTTTTG</u> |
| +6 (pKV53, pKV65, pKV66) | TTTACAACAA | | ATATAAAACA | | ATGTCTCAAA | | <u>AGATCTTTTG</u> |

The underlined region represents the DNA sequence of the BglII synthetic oligonucleotide linker.

FIG. 4

5' Non-Coding Region of pDB4 and the Hybrid PGK-GAL-UAS Promoter Constructs pDB4

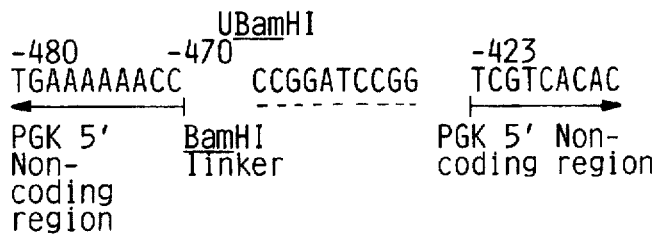

```
              UBamHI
-480      -470            -423
TGAAAAAACC      CCGGATCCGG    TCGTCACAC
|---------|    |----------|  |--------|
PGK 5'         BamHI         PGK 5' Non-
Non-           linker        coding region
coding
region
```

Plasmids: pKV43, pKV49, pKV61, pKV63, pKV65.

```
-480
TGAAAAAACC   CCGGATCTTT   TGAATTCCCA   CGGATTAGAA   GCCGCCGAGC

GGGTGACAGC   CCTCCGAAGG   AAGACTCTCC   TCCGTGCGTC   CTCGTCTTCA

CCGGTCGCGT   TCCTGAAACG   CAGATGTGCC   TCGCGCCGCA   CTGCTCCGAA

CAATAAAGAT   TCTACAATAC   TAGGGGGATC   CGGTCGTCAC   ACAAC------
                                BamHI
```

Plasmids: pKV44, pKV50, pKV62, pKV64, pKV66.

```
         BamHI
-480     |
TGAAAAAACC   CCGGATCCCC   TAGTATTGTA   GAATCTTTAT   TGTTCGGAGC

AGTGCGGCGC   GAGGCACATC   TGCGTTTCAG   GAACGCGACC   GGTGAAGACG

AGGACGCACG   GAGGAGAGTC   TTCCTTCGGA   GGGCTGTCAC   CCGCTCGGCG
                                                    -420
GCTTCTAA     TCCGTGGGAA   TTCAAAAGAT   CCGGTCGTCA   CACAAC——
```

Legend to Figure 5

Numbers indicate the relative position in the 5' non-coding region of the PGK gene.

The region bounded by arrows represents the GAL-UAS DNA sequence (Johnston & Davis, 1984).

The underlined region indicates the DNA sequence corresponding to the synthetic BglII oligonucleotide linker. The DNA sequence underlined by the broken line indicates the nucleotides derived from the synthetic BamHI oligonucleotide linker in pDB4.

FIG.5

HYBRID GAL10/PGK YEAST PROMOTER

CROSS-REFERENCE TO RELATED APPLICATIONS

This application is a continuation of application Ser. No. 07/853,865, filed Mar. 20, 1992, now abandoned, which is a continuation of application Ser. No. 07/577,815, filed Sep. 4, 1990, now abandoned, which is a continuation of application Ser. No. 07/089,987, filed Aug. 27, 1987, now abandoned.

This invention relates to the field of recombinant DNA technology. In particular it relates to a novel yeast promoter.

Recombinant DNA technology makes it possible to express heterologous gene products in *Saccharomyces cerevisiae*. This is achieved by constructing gene fusions between appropriate non-coding regulatory DNA sequences and the DNA sequence encoding the structural protein to be expressed. In this respect the 5' and 3' non-coding regions of the phosphoglycerate kinase (PGK) gene of *S. cerevisiae* have been used to construct expression vectors capable of synthesizing commercially important polypeptides in yeast (Tuite et. al., 1982; Kingsman & Kingsman, 1982; Mellor et. al., 1983). However, although these vectors are able to direct the synthesis of significant quantities of heterologous polypeptides in yeast, they are subject to the same physiological factors which influence the expression of the native yeast protein.

Thus, for example, when cells are grown in a medium supplemented with a fermentable carbon source, such as glucose, PGK promoter-directed expression is 20-30 fold higher than that observed when cells are grown in a medium containing a non-fermentable carbon source (Tuite et. al., 1982). This regulation of gene expression is mediated at the level of DNA transcription (Holland & Holland, 1978) and can be attributed to the properties of the 5' non-coding region of the PGK gene. This 5' non-coding region can be divided into functional domains which have similar properties to those observed in other 5' non-coding regions of yeast genes. In particular, a DNA sequence has been identified between nucleotides −324 and −445 which has the ability to activate DNA transcription when located upstream of a yeast 5' non-coding region (Kingsman & Kingsman, 1984). This DNA sequence, referred to as the PGK upstream activation sequence (UAS) is essential for the transcriptional activation of the PGK gene (Kingsman & Kingsman, 1984).

An analogous situation exists for the activation of other yeast genes. For example GAL1 and GAL10 of *S. cerevisiae* are activated by an UAS which confers galactose regulation of gene transcription (Guarente et. al., 1982; Johnston & Davis, 1984). This UAS we refer to as the GAL10 UAS. The GAL10 UAS can also be located upstream of other yeast gene 5' non-coding regions where it confers galactose regulation on DNA transcription (Guarente et. al., 1982).

The PGK 5' non-coding region is generally considered to be an extremely strong yeast promoter capable of mediating high level gene expression under optimal physiological conditions, i.e. when cells are grown in the presence of a fermentable carbon source. Whilst PGK expression can be regulated by a judicious choice of carbon source, expression is not subject to absolute control since significant levels of gene transcription occur in the presence of non-fermentable substrates. Consequently, the PGK promoter can not be used for the efficient regulation of heterologous gene expression in yeast.

Moreover, the PGK promoter is inappropriate for application within the context of European Patent Application No: 86303039.1, published under No 0201239. This application relates to the production of ethanol and a heterologous protein or peptide by fermenting an aqueous carbohydrate—containing medium with a yeast such as brewer's yeast which has been genetically modified to be capable of expressing a heterologous protein or peptide under conditions such that the yeast multiplies but no expression of the protein or peptide occurs, recovering the ethanol so formed, inducing expression of the protein or peptide by the yeast and obtaining the protein or peptide therefrom. Galactose regulation of expression of the heterologous gene is particularly useful here, since the medium in which the yeast is grown, brewers wort, does not normally possess sufficient galactose to induce the transcriptional activation and thus expression of galactose-regulated genes. Furthermore, genes which normally are regulated by galactose exhibit a high degree of inducible control. Thus, for example, when cells are either resuspended and/or grown in a medium supplemented with galactose, galactose-regulated transcription is approximately 1000-fold higher than that observed in the absence of galactose (Hopper et. al., 1978; St. John & Davis, 1979). This high level of induction is in contrast to that described earlier for PGK promoter-directed expression, which is only 20-30 fold inducible. However, whilst galactose-regulated gene expression enables a high degree of inducible gene regulation, it does not necessarily result in a concomitant high level of gene expression under fully induced conditions.

We now provide a hybrid yeast promoter comprising components of the 5' non coding region of the PGK gene and regulatory components from the GAL10 UAS. This has the advantage of conferring galactose regulation of gene transcription upon a modified 5' non-coding region of the inherently efficiently expressed PGK yeast gene. This results in the formation of a hybrid promoter which confers high level transcriptional activity in the presence of galactose, that is, under fully induced conditions, but low level (barely detectable) activity in the absence of galactose. Thus the hybrid promoter possesses the transcriptional activity of the PGK gene and the regulatory properties of the galactose regulated gene.

The new hybrid promoter comprises the GAL10 UAS fused to a modified 5' non-coding region sequence of the PGK gene and does not incorporate the endogenous PGK UAS. It is preferred that the GAL10 UAS is provided at the deletion site of the PGK UAS. The GAL10 UAS may be present in either orientation.

The hybrid promoter may be prepared by inserting the GAL10 UAS into a suitable site in the 5' non-coding region of the PGK gene. The 144 base-pair Rsa I–Alu I DNA fragment derivable from the GAL1–GAL10 promoter may be inserted.

Yeast expression vectors, typically plasmids, incorporate the hybrid promoter to control the expression of heterologous or homologous proteins or peptides. A wide range of heterologous proteins or peptides may be expressed. By way of example, mention may be made of enzymes such as beta-lactamase, beta-glucanase and beta-galactosidase. Other useful heterologous proteins and peptides include materials of human origin and/or useful in therapy, such as human serum albumin and immunoglobulins.

An expression vector may be constructed by inserting in a vector incorporating the hybrid promoter a gene coding for the protein or peptide which it is desired to express. The gene can be inserted at a restriction site which is provided downstream of the translational start codon controlled by the hybrid promoter. The gene must be inserted in the correct translational reading frame. A fusion product containing the protein or peptide of interest will then be expressed. Alternatively, the gene may itself be provided with a translational start codon followed directly by a DNA sequence encoding the protein or peptide of interest. Such a gene may be inserted in a vector incorporating the hybrid promoter but which does not incorporate a translational start codon. In such a vector, a restriction site is so provided that into the site the gene may be inserted in the correct reading frame and such that its translational start codon is correctly positioned in relation to the hybrid promoter. The expression vector is provided with a transcription terminator sequence. This may be the PGK terminator sequence.

The expression vectors can be used to direct the galactose-regulated high level expression of genes in a transformant yeast. The vectors may be used to transform laboratory strains of Saccharomyces cerevisiae. They may be used to transform industrial strains of Saccharomyces cerevisiae such as the top fermenting ale yeasts (S. cerevisiae) and the bottom fermenting lager yeasts (S. uvarum or S. carlsbergensis). The expression vectors are particularly useful for transforming brewer's yeast and can be used to provide galactose regulation of the process for the production of heterologous proteins and peptides according to European Application No. 86303039.1 as described above.

A peptide or protein may be obtained from the transformed yeast by growing and/or placing the yeast in a galactose-containing medium to switch on high level expression of the peptide or protein. Thus, a peptide or protein may be prepared by growing and/or placing in a galactose-containing medium a yeast which has been transformed by a yeast expression vector in which the expression of the said peptide or protein is controlled by a hybrid promoter of the invention and obtaining the said peptide or protein thus produced.

The following Example illustrates the invention. In the accompanying drawings:

BRIEF DESCRIPTION OF THE DRAWINGS

FIG. 4 shows the Bal 31 deletion series of pDB4;

FIG. 5 shows the 5' non-coding region of pDB4 and the hybrid PGK-GAL UAS promoter constructs.

EXAMPLE

Materials and Methods

Strains, Media and Transformations

Figure 1:
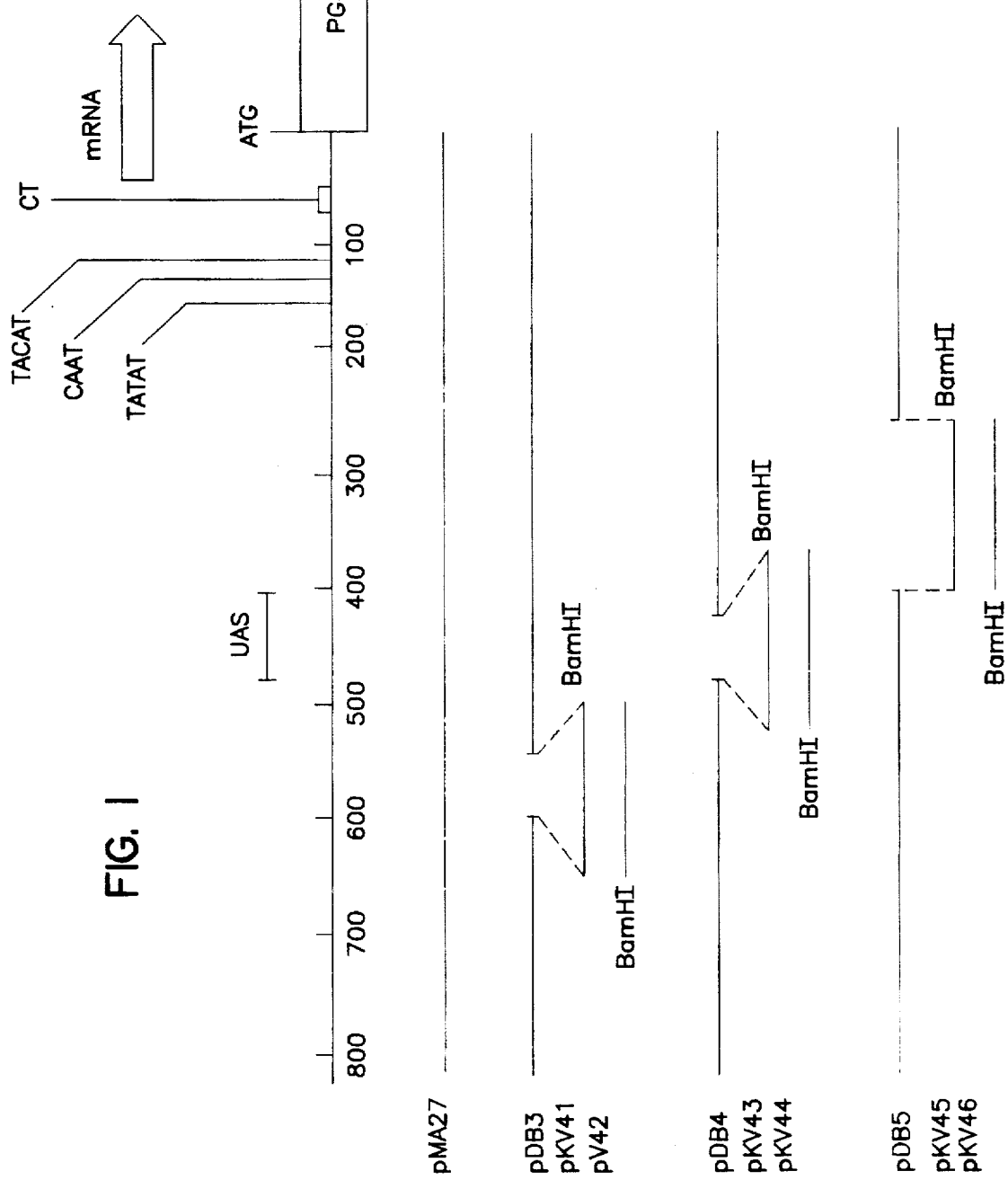
FIG. 1 shows the location of GAL10 UAS insertions in the 5' non-coding region of the PGK gene.

Strains used were E. coli AKEC 28 (C600, thrC, leuB6, thyA, trpC117, hsdR$_k$, hsdM$_k$) and S. cerevisiae DBY745 (α, ura3-52, ade1-100, leu2-3, leu2-112).

E. coli cultures were grown on LB medium (Miller, 1972) supplemented where appropriate with the antibiotic ampicillin (Sigma Chemical Co. Ltd., Poole, Dorset, England.) at 50 µg/ml final concentration. Yeast were grown at 30° C. on a synthetic complete medium (SC) (0.67% w/v yeast nitrogen base without amino acids) supplemented with carbon source and amino acids where appropriate.

E. coli was transformed using standard methods (Maniatis, et. al., 1982). Yeast was tranformed as described by Hinnen et. al., (1978), Recombinant DNA Techniques.

Standard procedures were used for restriction endonuclease digestion and the construction of plasmid DNA (Maniatis et. al., 1982). All enzymes were obtained from Bethesda Research Laboratories (Paisley, Scotland) and were used according to the manufacturers recommendations. Exonuclease Bal31 was used for the in-vitro deletion of DNA sequences as described by Dobson et. al., (1982). Deletion end-points were determined by DNA Sequencing (Sanger et. al. 1977; Maxam & Gilbert, 1980). BgLII synthetic oligonucleotide linkers were obtained from Collaborative Research Inc. (Lexington, Mass., USA).

DNA & RNA Isolation

Plasmid DNA was isolated from E. coli by the methods of Chinault and Carbon (1979) and Birnboim and Doly (1979). The method of Holmes & Quigley (1981) was used for the rapid analysis of plasmid DNA. Total yeast DNA was prepared according to Cryer et. al., (1975). Total RNA was prepared from yeast cells grown to a density of $4 \times 10^6$ cells ml$^{-1}$ as described previously (Dobson et. al., 1982).

Hybridisation and DNA probes

Northern and Southern transfers were performed using standard procedures (Maniatis et. al., 1982). Hybridisation of $^{32}$PdTTP (Amersham International Ltd., Amersham) nick translated (Rigby et. al., 1977) DNA probes was performed according to Thomas (1980). PGK (Mellor et. al., 1983), Ty (Dobson et. al., 1984) and rDNA (Petes et. al., 1978) DNA probes were labelled to a specific activity of $4-6 \times 10^7$ cpm/µg DNA following purification from agarose gels (Tabak & Flayell, 1978).

Determination of plasmid copy number and RNA analysis

Total yeast DNA was digested with the restriction endonuclease EcoRI and separated by electrophoresis in a 1% w/v agarose gel. DNA fragments were transferred to nitrocellulose and hybridized to radioactively labelled PGK and rDNA specific DNA probes to estimate plasmid copy number. Regions of DNA homology were highlighted by autoradiography. By comparing the relative intensity of the rDNA and PGK specific regions of homology it was possible to estimate the number of copies of the PGK specific DNA sequence. This was facilitated by the knowledge that there are approximately 100-140 repeats of the genomic rDNA per haploid genome (Petes et. al., 1978). This method of plasmid copy number determination is generally applicable providing that an appropriate plasmid DNA probe is utilized in the assay.

Total RNA was separated by electrophoresis in 1% w/v agarose containing 6% w/v formaldehyde. RNA was transferred to nitrocellulose filters as described previously and hybridized with nick translated DNA probes. A transposon Ty mRNA species of 5700 nucleotides or a ribosomal DNA probe of 1800 nucleotides was used as an internal loading control in hybridizations to enable a direct comparison between different transformants.

Results

Analysis of the 5' non-coding region of the PGK gene

A series of deletion 'windows' have been constructed in the 5' non-coding region of the yeast PGK gene (FIG. 1).

These were obtained by ligating a combination of DNA fragments possessing deletions in to the 5' non-coding region of the PGK gene from both the 5' and the 3' direction. 5' to 3' deletions were obtained in a derivative of plasmid pMA27 (Mellor et. al., 1983) in which the Cla I site at position −800 in the PGK 5' non-coding region had first been converted to a unique Xho I restriction site using a synthetic oligonucleotide linker. This pMA27 derivative was then cleaved with Xho I and digested with Bal 31 exonuclease. Plasmids were recircularized by ligation in the presence of Bam HI synthetic oligonucleotide linkers and transformed into E. coli. Plasmid DNA was isolated and the positions of the 3' deletion end-points were characterised by DNA sequencing. 3' to 5' deletions were obtained in plasmid pMA22a (Dobson et. al., 1982), following cleavage at the unique Bam HI site and Bal 31 exonuclease digestion. Plasmids were recircularized by ligation in the presence of Bam HI synthetic oligonucleotide linkers and transformed into E. coli. Plasmid DNA was isolated and the positions of the 5' deletion end-points were similarly characterized by DNA sequencing. Plasmids pDB3, pDB4 and pDB5 (FIG. 1) were then constructed by ligating Bam HI-Pst I fragments containing appropriate combinations of the 5' and 3' deletion derivatives. Thus DNA sequences downstream of the 3' end-points were obtained from the 5' deletion derivatives, whereas DNA sequences upstream of the 5' end-points were obtained from the 3' deletion derivatives.

Plasmids pDB3 and pDB5 possess deletions which are located 5' and 3' of the PGK UAS respectively, whereas pDB4 has a deletion between coordinates −423 and −470 which includes the (see FIGS. 1 and 5). Each of the aforementioned plasmids was constructed such that a unique Bam HI restriction site bounded the deletion end-points. This facilitates subsequent DNA insertions.

Yeast transformed with plasmids pMA27, pDB3 and pDB5 produces comparable high levels of PGK mRNA when grown on SC supplemented with various carbon sources, whereas yeast harbouring plasmid pDB4 produces levels of PGK mRNA equivalent to those produced by the untransformed yeast. This indicates that the PGK UAS is essential for PGK mRNA synthesis.

Construction of a galactose inducible PGK based gene

Figure 2:
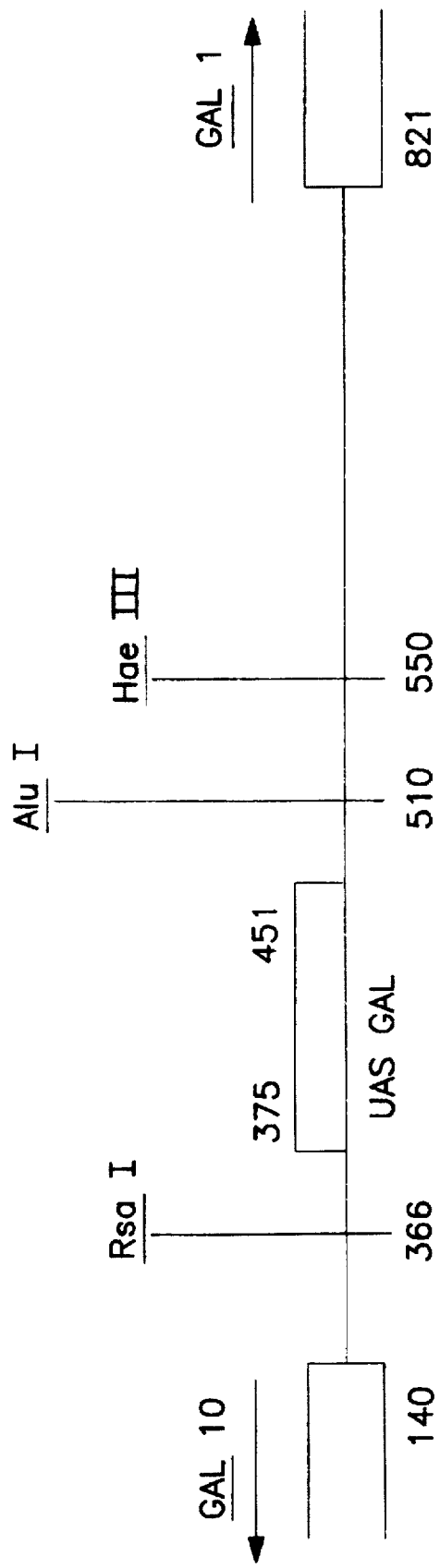
FIG. 2 is a diagrammatic representation of the divergent GAL1-GAL10 promoter region of S. cerevisiae.
Figure 3:
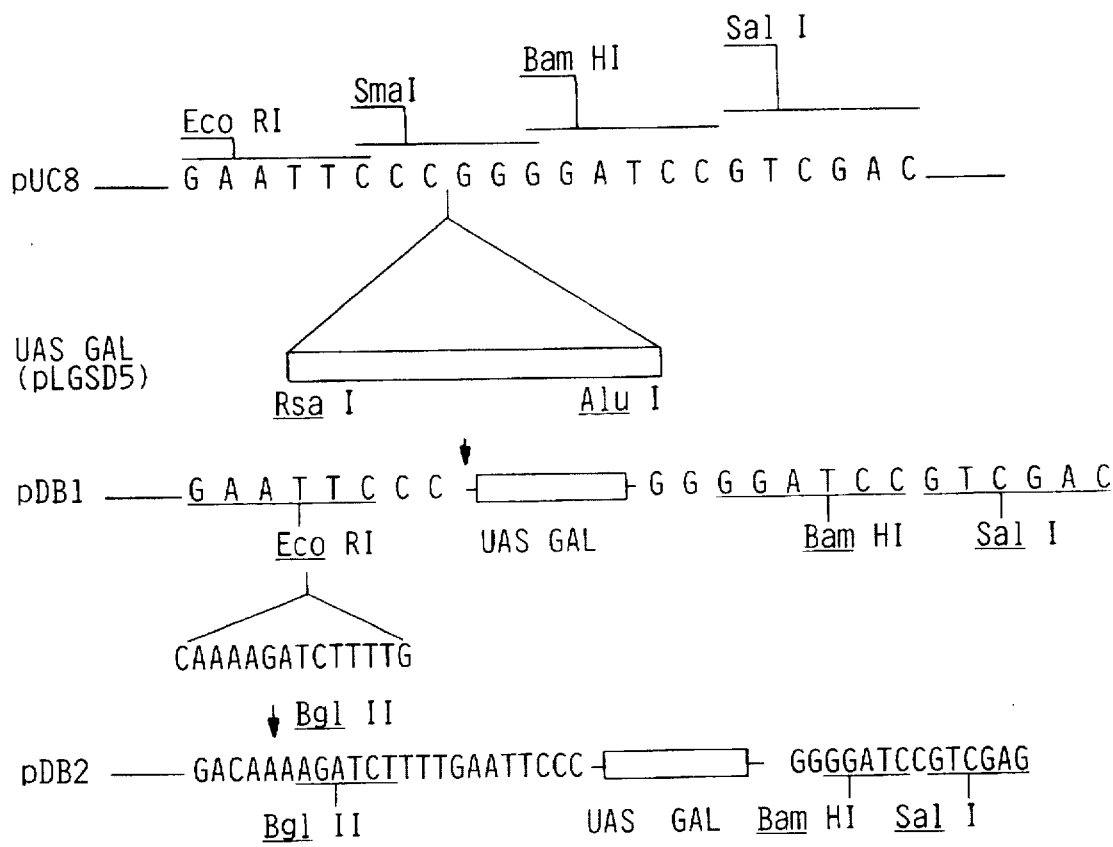
FIG. 3 illustrates the construction of plasmids pDB1 and pDB2.

The organization of the GAL1-GAL10 divergent promoter of yeast is shown schematically in FIG. 2. The functional region of the UAS has been localized (West et. al., 1984) and its position is indicated along with flanking restriction sites (FIG. 2). A 365 base-pair DNA fragment is to be found on plasmid pLGSD5 (Guarente et. al., 1982) which carries the GAL10 UAS. The 144 base-pair Rsa I-Alu I DNA fragment from the GAL1-GAL10 promoter region on pLGSD5 was purified from a polyacrylamide gel and blunt-end ligated into the unique Sma I site of pUC8 (FIG. 3). Subsequently, the unique Eco RI site of pDB1 (FIG. 3) was converted to a BgL II site by the insertion of a synthetic BgL II oligonucleotide linker. Thus the 144 base-pair GAL10 UAS could be isolated on a unique BgL II-Bam HI DNA fragment carried by plasmid pDB2 (FIG. 3). This fragment was subsequently cloned into the unique Bam HI site in each of the three PGK deletion vectors pDB3, pDB4 and pDB5; GAL10 UAS inserts were obtained in either orientation to derive plasmids designated pKV41-pKV46 (FIG. 1).

Plasmids pKV43, pKV44, pMA27 and pDB4 were transformed into strain DBY745 and the levels of PGK specific mRNA were determined during exponential growth on media containing either glucose or galactose as carbon source. The results indicated, in the case of pKV43 and pKV44 that PGK specific mRNA could be induced to high levels in the presence of galactose, whereas growth on glucose resulted in chromosomal levels of PGK specific mRNA. Transformants harbouring plasmid pMA27 showed high levels of PGK specific mRNA when grown on both glucose and galactose medium, however pDB4 showed no activity on either carbon source. These results clearly demonstrate that the replacement of the PGK UAS with the GAL10 UAS, in either orientation, confers high level galactose regulated DNA transcription on the PGK promoter. Transformants harbouring plasmids pDB3 and pDB5 maintained high levels of PGK specific mRNA on both glucose and galactose medium, comparable to that from plasmid pMA27. In the case of plasmids pKV41, pKV42, pKV45 and pKV46 high levels of PGK specific mRNA are maintained on both carbon sources. These results show that it is not sufficient to insert the GAL UAS at any site 5' of the transcription initiation sequence of PGK in order to confer galactose regulation upon transcription, but rather it is necessary both to insert the GAL UAS and to remove the PGK UAS. Thus in the case of pKV43 and pKV44 the PGK UAS has been deleted and replaced by the GAL UAS.

Construction of a galactose regulated PGK expression vector

Plasmid pDB4 was digested at a unique Bgl II site located in the 3' region of the PGK structural gene and the linear molecule was digested with Bal 31 exonuclease (FIG. 4). DNA fragments were filled-in and re-ligated in the presence of excess BgL II synthetic oligonucleotide linkers; plasmids thus formed were screened by gel electrophoresis and DNA sequencing to determine the precise 'end-point' of the deletion. A series of deletion derivatives were obtained differing in the nucleotide sequence immediately 5' of the BgL II linker. Deletion derivatives with 'end-points' at positions −8 (pKV47), +4 (pKV51), +5 (pKV52) and +6 (pKV53) were obtained (FIG. 4).

The deletion derivatives were further modified by the attachment of the 3' transcription terminator sequence of the PGK gene. This was accomplished by digesting each plasmid with the restriction endonucleases BgL II and Pst I and ligating the large fragment thus generated with the small Bam HI-Pst I fragment containing the 3' transcription terminator sequence of the PGK gene derived from plasmid pMA91 (Mellor et. al., 1983). Plasmids thus formed were then further modified by the insertion at the unique Bam HI site in the modified 5' non-coding region of the PGK gene of the BgL II-Bam HI fragment containing the GAL 10-UAS from pDB2 (FIG. 3.). The orientation of insertion of the GAL 10-UAS was then determined by restriction enzyme digestion analysis to produce plasmids indicated in FIG. 5.

In this manner a series of galactose regulated PGK expression vectors were obtained in which the PGK-UAS had been replaced by the GAL10 UAS. The DNA sequence surrounding position 1 of the PGK coding region for each of these vectors is depicted in FIG. 4. Whereas, the DNA sequence of the modified PGK 5' non-coding region into which the GAL10 UAS has been inserted is presented in FIG. 5.

Expression vectors pKV49 and pKV50 (FIGS. 4 and 5) can be used to mediate the expression of heterologous and homologous genes in which the 5' translational initiation signal (ATG) is supplied by the gene of interest. Under circumstances in which the gene to be expressed does not possess a 5' translational initiation signal (ATG), translational fusion vectors can be used. In this respect deletions in the PGK coding sequence ending at positions +4, +5 and +6 (FIG. 4) facilitate fusion of the gene to be expressed into each of the three possible reading frames. These deletion derivatives have been used in the construction of expression vectors pKV61–66. Plasmids pKV61 and pKV62, pKV63 and pKV64, pKv65 and pKV66, are analogous to pKV49 and pKV50 respectively in respect of the orientation of the GAL10 UAS (FIG. 5).

The expression of human serum albumin in yeast

Figure 6:
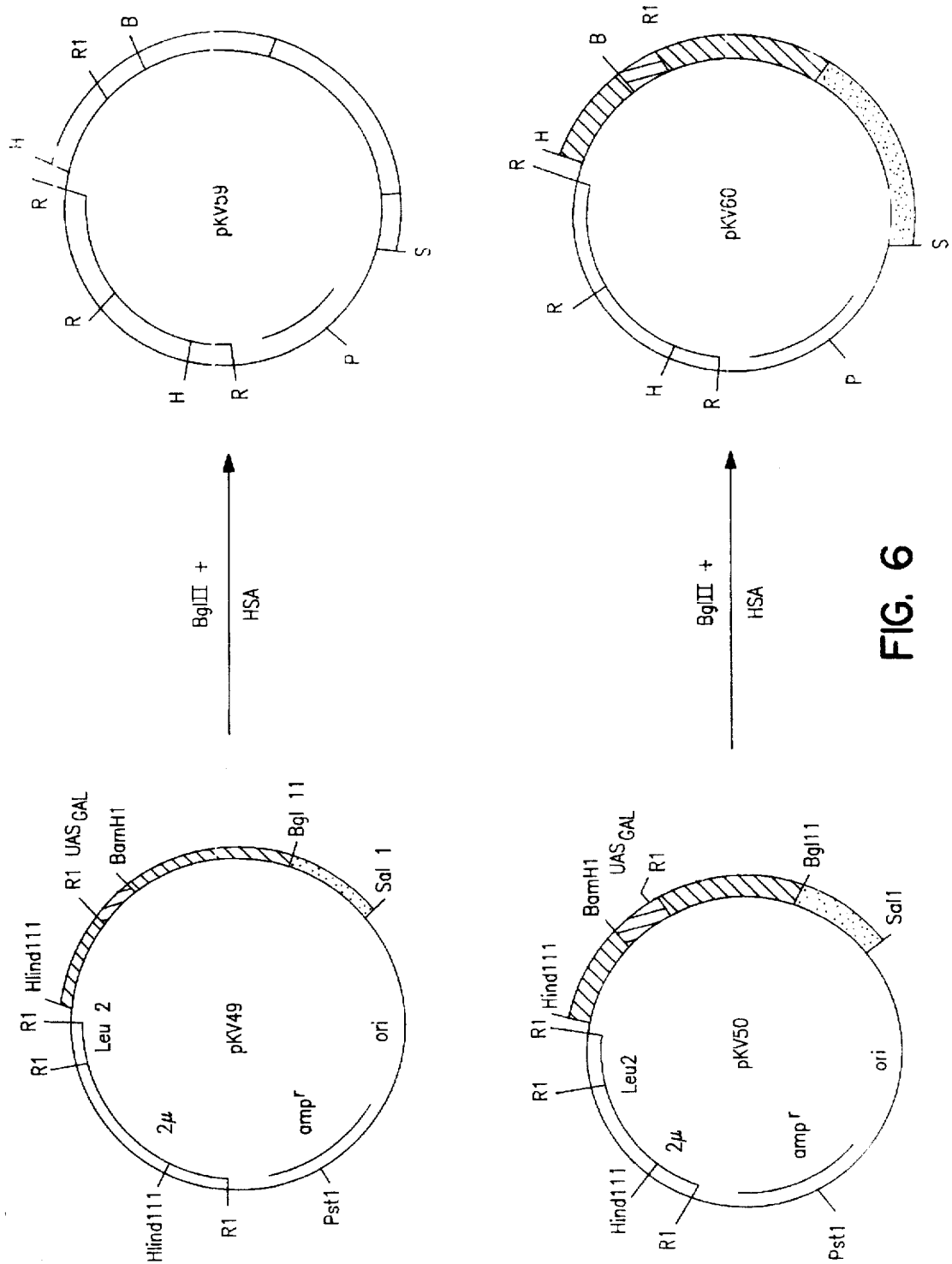
FIG. 6 shows the generation strategy of plasmids pKV59 and pKV60.
Figure 7:
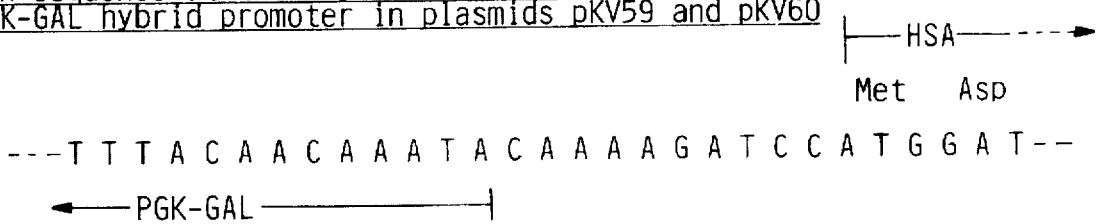
FIG. 7 shows the DNA sequence at the 5' junction of the HSA gene and the PGK-GAL hybrid promoter in plasmids pKV59 and pKV60.

A cDNA clone encoding the human serum protein albumin (HSA) was isolated on a 1.84 kilo-base-pair BamHI DNA fragment from plasmid pEK113 (described in European Patent Publication No. 0201239A in the name of Delta Biotechnology Ltd.) and subcloned into the unique BgLII site of the expression vectors pKV49 and pKV50 (FIGS. 4 and 5) to generate plasmids pKV59 and pKV60 respectively (FIG. 6). This HSA encoding DNA sequence had previously been manipulated to include a 5' translational initiation signal immediately adjacent to the first codon of the mature HSA coding sequence (European Patent Publication No. 0201239A). The DNA sequence at the 5' junction of the HSA gene with pKV49 and pKV50 is indicated in FIG. 7.

Figure 8:
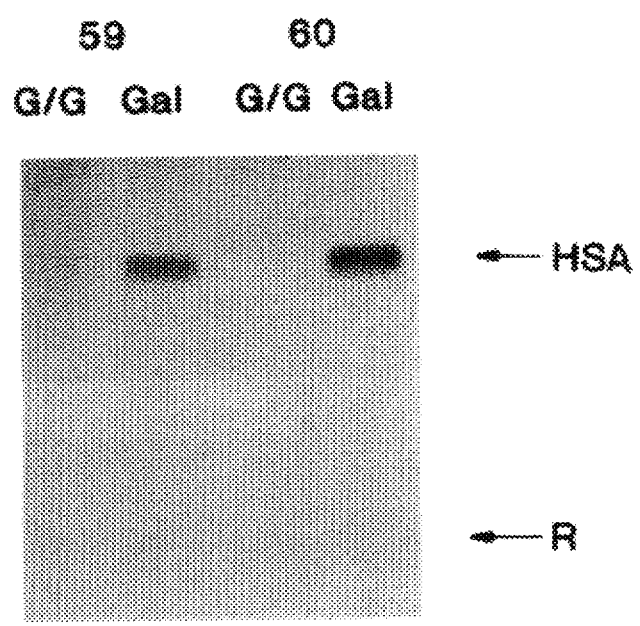
FIG. 8 shows an autoradiograph of a Northern blotted total yeast RNA isolated from DBY745 (pKV59) and DBY745 (pKV60).

Plasmids pKV59 and pKV60 were transformed into the laboratory yeast strain DBY745 by standard procedures. Transformants were subsequently grown on SC supplemented with adenine and uracil plus either glucose (1% w/v) and galactose (1% w/v) or galactose (1% w/v), representing repressing and inducing carbon sources respectively. Cultures were harvested at a cell density of 4–6×10$^4$ per ml and used to prepare extracts of total DNA, total RNA and protein. The results presented in FIG. 8 clearly show that galactose induces the synthesis of HSA specific mRNA, whereas in the presence of glucose little or no HSA specific mRNA can be detected. Cell extracts were also assayed for HSA protein following SDS:polyacrylamide gel electrophoresis and Western blotting (European Patent Publication No. 0201239A). The results of these gels were consistent with the mRNA analyses described above since substantial quantities of HSA could be detected in yeast grown in the presence of galactose, whereas yeast grown in the presence of glucose produced much lower, but detectable quantities of HSA. When protein bands on SDS:polyacrylamide gels were visualized following coomassie blue staining, a significant proportion of the total cellular protein was constituted by the HSA protein in the galactose induced cultures, whereas no HSA band could be visualized in cultures grown in the presence of glucose.

References

Birnboim, A. C. & Doly, J. (1979), Nucleic Acids Research, 7, 1513–1523.
Chinault, A. C. & Carbon, J. A. (1979), Gene, 5, 111–126.
Dobson, M. J. et. al. (1982), Nucleic Acids Research, 10, 2625–2637.
Dobson, M. J. et. al. (1984), EMBO Journal, 3, 1115–1121.
Guarente, L. (1984), Cell, 36, 799–800.
Guarente, L. et. al. (1982), Proceedings of the National Academy of Sciences, USA, 79, 7410–7414.
Guarente, L. Mason, T. (1983), Cell, 32, 1279–1286.
Hinnen, A. et. al. (1978), Proceedings of the National Academy of Sciences, USA, 75, 1929–1933.
Holland, M. J. & Holland, J. P. (1978), Biochemistry, 17, 4900–4907.
Holmes, D. S. & Quigley, F. A. (1981), Annals of Biochemistry, 114, 193–197.
Johnston, M. & Davis, R. W. (1984), Proceedings of the National Academy of Sciences, USA, 75, 2878–2882.
Hopper, J. E. et. al. (1978), Molecular and Cellular Biology, 4, 1440–1448.
Kingsman, A. J. & Kingsman, S. M. (1982), European Patent Application No: 82304460.7.
Kingsman, A. J. & Kingsman, S. M. (1984), International Patent Application No: PCT/GB84/00189(WO 84/04757)
Maniatis T. et. al. (1982), Molecular Cloning. A laboratory Manual, Cold Spring Harbor Laboratory, Cold Spring Harbor, N.Y.
Maxam, A. M. & Gilbert, W. (1980), Methods in Enzymology, 65, 499–560.
Mellor, J. et. al. (1983), Gene, 24, 1–14.
Miller, J. H. (1972), Experiments in Molecular Genetics, Cold Spring Harbor Laboratory, Cold Spring Harbour, N.Y.
Petes, T. D. et. al. Journal of Bacteriology, 134, 295–305.
Rigby, P. J. W. et al. (1972), Journal of Molecular Biology, 113, 237–251.
Sanger, F. et. al. (1977), Proceedings of the National Academy of Sciences, USA, 74, 5463–5467.
Sarokin, L. & Carlson, M. (1984), Molecular and Cellular Biology, 5, 2521–2526.
St. John, T & Davis, R. (1979), Cell, 16, 443–452.
Struhl, K. (1982), Proceedings of the National Academy of Sciences, USA, 79, 7385–7389.
Struhl, K. (1984), Proceedings of the National Academy of Sciences, USA, 81, 7865–7869.
Tabak, H. F. & Flayell, R. A. (1978), Nucleic Acids Research, 5, 2321–2332.
Thomas, P. (1980), Proceedings of the National Academy of Sciences, USA, 77, 5201–5202.
Tuite, M. F. et. al. (1982) EMBO Journal 1, 603–608.
West, R. W. et. al. (1984), Molecular and Cellular Biology, 4, 2467–2478.

We claim:

1. A hybrid yeast promoter comprising the upstream activation sequence of the Saccharomyces cerevisiae GAL10 gene operably linked to a downstream sequence effective in promoting transcription of a coding sequence placed downstream thereof, wherein the downstream transcription promoting sequence is a Saccharomyces cerevisiae phosphoglycerate kinase (PGK) promoter sequence, and wherein the hybrid yeast promoter does not contain the upstream activation sequence of the Saccharomyces cerevisiae PGK promoter which is located between nucleotides −470 and −423 relative to the translational start site of the PGK gene.

2. The hybrid yeast promoter according to claim 1, wherein the upstream activation sequence of the Saccharomyces cerevisiae PGK promoter sequence has, at the same location, been substituted with the upstream activation sequence of the Saccharomyces cerevisiae GAL10 gene.

3. A yeast expression vector comprising the hybrid yeast promoter according to claim 1.

4. The yeast expression vector according to claim 3, further comprising a translational start codon operably linked to said hybrid yeast promoter and a restriction site downstream of said start codon such that a gene to be expressed, when inserted into said restriction site, will be in the same and continuous translational reading frame as said start codon.

5. The yeast expression vector according to claim 3, which does not contain a translational start codon at the translational start site controlled by said hybrid yeast promoter and further which contains a restriction site such that a gene which possesses a translational start codon, when inserted into said restriction site, will be operably linked to the hybrid yeast promoter.

6. A yeast transformed with the vector according to claim 5.

7. The yeast expression vector according to claim 3, further comprising a Saccharomyces cerevisiae gene operably linked to the hybrid yeast promoter.

8. The yeast expression vector according to claim 3, further comprising a gene operably linked to the hybrid yeast promoter, which gene is not a *Saccharomyces cerevisiae* gene.

9. The yeast expression vector according to claim 8, in which the gene operably linked to the hybrid yeast promoter encodes human serum albumin.

10. A yeast transformed with the vector according to claim 9.

11. A yeast transformed with the vector according to claim 3.

12. The yeast according to claim 11, which is a transformed brewer's yeast.

13. A process for preparing a polypeptide or protein comprising maintaining in a galactose-containing medium a yeast transformed with a yeast expression vector in which the expression of the polypeptide or protein is controlled by the hybrid yeast promoter of claim 1 thereby producing the polypeptide or protein, and recovering the polypeptide or protein thus produced.

* * * * *